United States Patent [19]

Charmot

[11] Patent Number: 5,128,204
[45] Date of Patent: Jul. 7, 1992

[54] MAGNETIZABLE MICROSPHERES BASED ON A POLYSILSESQUIOXANE AND A PROCESS FOR THEIR PREPARATION

[75] Inventor: Dominique Charmot, Paris, France
[73] Assignee: Rhone-Poulenc Chimie, Cedex, France
[21] Appl. No.: 634,908
[22] Filed: Dec. 27, 1990

[30] Foreign Application Priority Data

Dec. 27, 1989 [FR] France ............... 89 17231

[51] Int. Cl.$^5$ .............................. B32B 5/16
[52] U.S. Cl. ................... 420/329; 428/402; 252/62.56
[58] Field of Search ............... 428/329, 402; 252/62.56

[56] References Cited

U.S. PATENT DOCUMENTS 3,480,555  11/1969  Jackson et al. ................. 252/62.56

FOREIGN PATENT DOCUMENTS 0125995  11/1984  European Pat. Off. .
1313846  11/1962  France .
  88676   1/1967  France .
1480409   4/1967  France .
2618084   1/1989  France .
2624873   6/1989  France .

OTHER PUBLICATIONS

PCT Application No. PCT/SE78/0001 entitled "Magnetic Polymer Particles".
PCT Application No. PCT/US86/02093 entitled "Magnetic-Polymer Particles".
Patent Abstracts of Japan, vol. 13, No. 579 (C-668)[3927], Dec. 20, 1989.

*Primary Examiner*—Edith L. Buffalow
*Attorney, Agent, or Firm*—Finnegan, Henderson, Farabow, Garrett and Dunner

[57] ABSTRACT

Magnetizable microspheres comprising a polysilsesquioxane network and, distributed within the network, a magnetizable filler chemically bonded to polysilsesquioxane units. The magnetizable microspheres are prepared by dispersing an aqueous suspension of a magnetizable filler, not coated with a dispersing agent, in a solvent, dissolving an alkoxysilane or an alkoxysiloxane in the organic phase, polycondensating to a polysilsesquioxane, removing water, separating, and optionally redispersing the microspheres in water.

14 Claims, No Drawings

MAGNETIZABLE MICROSPHERES BASED ON A POLYSILSESQUIOXANE AND A PROCESS FOR THEIR PREPARATION

The present invention relates to magnetizable microspheres based on a matrix of polysilsesquioxane and magnetizable fillers distributed uniformly inside said matrix, and a process for the preparation of said microspheres. The present invention also relates to application of said magnetizable microspheres, particularly to biology.

In French Patent Application No. 2,618,084, the assignee of the present invention described magnetizable composite particles consisting of a matrix based on straight-chain organopolysiloxane and, encapsulated in said matrix, magnetizable fillers. The preparation of these types of particles involves the use of a magnetic fluid (ferrofluid), the magnetic fillers of which are coated with a dispersing agent, rendered insoluble in water by thermal decomposition.

Applicant's French Patent Application No. 2,624,873 discloses magnetizable particles consisting of a matrix originating from the hydrosilylation of an organopolysiloxane SiVi and a hydrogenopolysiloxane SiH and, encapsulated in said matrix, magnetizable fillers coated with a dispersing agent and rendered insoluble in water by thermal decomposition.

The preparation of these two types of particles involves magnetizable fillers, the surface of which is coated with a dispersing agent rendered insoluble in water. The presence of this dispersing agent can be a drawback for use in biology because this agent can migrate towards the surface of the particles, and give rise to side reactions.

The Applicant has now found magnetizable microspheres, the magnetizable filler of which is not coated with a hydrophobic surfactant, said filler being distributed in a homogeneous manner within a silicone matrix.

Applicant's invention concerns magnetizable microspheres comprising:

a matrix based on a polysilsesquioxane network; and
a magnetizable filler uniformly distributed inside said network and chemically bonded to silsesquioxane units, said filler having a size preferably smaller than $300 \times 10^{-4}$ μm, more preferably about $50 \times 10^{-4}$ to $120 \times 10^{-4}$ μm; said microspheres having a BET specific surface area preferably about 2 to 50 m²/g, more preferably about 2 to 10 m²/g.

The polysilsesquioxanes can be represented by the unit formula $R-Si-O_{3/2}$ and obtained by polycondensation of an alkoxysilane of the formula:

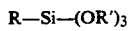   (I)

or an alkoxysiloxane of the formula:

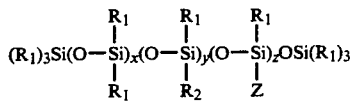   (II)

in which formulae:

$R_1$ is selected from a $C_1-C_3$ alkyl radical, preferably methyl or ethyl, and a phenyl radical;

$R_2$ is selected from a radical $R_1$ defined above, a $C_1-C_4$ alkyl radical substituted by, for example, amino, epoxy, mercapto, or halogeno groups, preferably aminopropyl, glycidylpropyl, mercaptopropyl, bromopropyl, chloropropyl, trifluoropropyl, and the like, and a vinyl radical;

R is selected from a radical $R_2$ defined above, an ethylenically unsaturated radical, preferably an unsaturated ester such as methacryloxypropyl, or a diorganopolysiloxy radical having from 4 to 20 diorganosiloxy groups;

OR' is selected from an OH radical and a hydrolyzable radical such as those in which R' represents:

a $C_1-C_4$ alkyl radical, or a $-CO-CH_3$, $-CO-C_2H_5$, $-CO-CH_2-CO-CH_3$, $-CH_2-CH_2OH$, $-CH_2CH_2-OCH_3$, or a $-CH_2-CH_2-OC_2H_5$ radical;

Z is a radical $-r-Si(R_1)_{3-n}(OR')_n$ in which r is a $C_1-C_{18}$, preferably a $C_2-C_6$, alkylene group and n is an integer from 0 to 3; and x, y and z have values sufficient to ensure a viscosity lower than 100 mPas at 25° C., preferably from 10 to 100 mPas at 25° C., wherein x or y can independently be zero.

Among the materials which can make up the magnetizable filler, the following may be mentioned by way of example: magnetite, hematite, chromium dioxide, the ferrites such as the manganese, nickel, and manganese-zinc ferrites. The preferred materials are magnetite and hematite. The magnetizable filler can also be a mixture of fillers. These materials can also be present as a mixture with a filler having a fluorescence spectrum such as yttrium oxide or oxysulphide activated with europium, gadolinium - cerium - terbium borate, cerium - terbium aluminate, magnesium - barium aluminate doped with divalent europium.

The amount of magnetizable filler corresponds to about 0.5% to 98%, of which 0.01% to 0.5% is made up of optional fluorescent filler, of the weight of the microspheres. The amount of magnetizable filler is preferably from 5 to 80% of the weight of the microspheres.

The magnetizable microspheres of Applicant's invention are substantially spherical. The magnetizable microspheres can be of uniform size or have a particle size variation. The diameter of the magnetizable microspheres is preferably about 0.05 to 3 μm and is more preferably about 0.2 to 2 μm.

The magnetizable microspheres of the invention are useful alone or as a dispersion in water. The amount of magnetizable microspheres in the dispersed state in water is preferably about 10 to 70% by weight relative to the total weight of dispersion, more preferably about 15 to 50% by weight.

The present invention also relates to a process for the preparation of the magnetizable microspheres described above.

The process comprises:

dispersing in an organic solvent immiscible with water, an aqueous suspension of a magnetizable filler, not coated with a dispersing agent, said filler having a size preferably smaller than $300 \times 10^{-4}$ μm, more preferably on the order of $50 \times 10^{-4}$ to $120 \times 10^{-4}$ μm;

dissolving, in the organic phase of the dispersion obtained, an alkoxysilane of formula I or an alkoxysiloxane of formula II, capable of undergoing polycondensation to form a polysesquioxane;

subjecting the alkoxysilane or alkoxysiloxane to polycondensation;

removing the water resulting from the polycondensation;

separating off the magnetizable microspheres; and if appropriate, redispersing said microspheres in water.

One preferred process comprises introducing all or part of an alkoxysilane or alkoxysiloxane into the aqueous suspension of the magnetizable filler before dispersing said aqueous suspension in the organic solvent.

The organic solvent used in the dispersion step is a solvent for alkoxysilanes of formula I or alkoxysiloxanes of formula II. The following solvents may be mentioned by way of example: cyclohexane, methylene chloride, benzene, hexane, toluene, carbon tetrachloride, octane, and esters of fatty diacids.

The dispersion step can be carried out in one or more steps at a temperature of about 20° to 60° C., with the aid of a vigorous agitation system, such as a colloid mill, high-pressure pumps, a vibratory stirrer, or ultrasonic equipment.

The aqueous suspension of magnetizable filler can be obtained by suspending a filler which has been ground up; however, a preferential form of suspension is an aqueous sol of magnetizable filler obtained by any known process, such as that described in U.S. Pat. No. 3,480,555.

Other fillers can be present along with the magnetizable filler, such as luminescent fillers.

The concentration of magnetizable filler in the aqueous suspension is preferably about 0.5 to 50% by weight, more preferably about 5 to 20% by weight. The amount of filler used is such that the ratio, by weight, of magnetizable filler to alkoxysilane or alkoxysiloxane is about 0.005:1 to 50:1.

The amount of organic solvent used is such that the ratio, by weight, of the aqueous phase to the organic phase is about 0.005:1 to 2:1.

A surfactant may be used to carry out the dispersion step. The surfactant is preferably chosen from those enabling the attainment of a water-in-oil emulsion having an HLB generally lower than 10 and preferably lower than 5. Such surfactants may be selected from nonionic agents such as fatty acid esters of sorbitol, sorbitan mono- and tri-oleates, ethylene oxide/propylene oxide block copolymers, ethoxylated alkylphenols containing less than 10 ethoxylated units, polycondensation products of fatty acids, and organosiloxane - ethylene oxide - propylene oxide block copolymers; anionic agents, such as dialkyl sulphosuccinates; and cationic agents, such as cetylammonium bromide and polyethyleneimine-polyester copolycondensation products.

The polycondensation step is preferably carried out at a temperature of about 20° to 80° C. for about 5 to 24 hours.

The water is then removed, for example, by distillation.

After cooling, the magnetizable microspheres can be separated from the organic medium by any known means, preferably by magnetization.

If desired, the magnetizable microspheres can be redispersed in deionized water until a proportion of solids of about 10 to 70% by weight, preferably about 15 to 50% by weight, is obtained. This step is preferably carried out in the presence of at least one surfactant, such as an alkyl sulphate and an alkylsulphonate, enabling the attainment of an oil-in-water emulsion having an HLB generally higher than 10, preferably higher than 15.

The magnetizable microspheres which are the subject of Applicant's invention are of particular value in biology.

The magnetizable microspheres can be used, for example, as active supports:

for antibodies or antigens for diagnostic tests and for the separation of biological compounds by affinity; the fixation of biological molecules can, if necessary, be carried out by well-known coupling methods involving coupling agents such as glutaraldehyde or water-soluble carbodiimide, or by activating any functional groups in the polyorganosiloxane (for example by diazotization, by the action of cyanogen bromide or hydrazine) and reacting the molecule to be fixed;

for enzymatic systems for biological reactions;

for fixation of cell cultures;

to guide medicaments or indicator substances towards the chosen point of treatment either in vitro or in vivo;

for chemical molecules enabling growth of these molecules by rapid sequences of individual reactions, such as peptide synthesis;

for reaction catalysts; or for the separation or the extraction of metals or optical isomers.

These microspheres can also be used as reinforcing fillers for elastomers or for the preparation of organic dispersions used in the hydraulic circuits of brakes and shock absorbers.

When said microspheres also contain a luminescent filler, said microspheres can be used as a cell marker or as a contrast agent in medical imagery.

The following examples are given by way of illustration and may not be regarded as limiting the field and the spirit of the invention.

An aqueous suspension of magnetic iron oxide, not treated with a surfactant, and used in the examples below, was prepared in the following way:

175 g of $Fe(NO_3)_3 \cdot 9H_2O$ and 75 g of $Fe(SO_4) \cdot 7H_2O$ were in 250 g of ion-exchanged water and 55 g of concentrated nitric acid; 250 g of a 20% aqueous solution of ammonia were added while stirring rapidly. After settling and removal of the supernatant solution, the precipitate was washed once with water. The mixture was then adjusted to pH 0.5 using 35 g of perchloric acid and the precipitate was filtered off; this operation was repeated 3 times, after which the oxide was taken up in suspension in water and subjected to ultrafiltration using ion-exchanged water. The suspension thus obtained had a solids content of 26.5% at a pH of 1.2. The yield, expressed as $Fe_3O_4$, was 57%. Examination by transmission electron microscopy indicated iron oxide particle sizes of between $50 \times 10^{-4}$ and $200 \times 10^{-4}$ microns.

EXAMPLE 1

Preparation of Magnetizable Microspheres Based on Poly(methyl)silsesquioxane 2 g of iron oxide suspension prepared as above were dispersed in a mixture comprising of 50 g of Solvesso 200 (polyaromatic petroleum cut supplied by Esso (France)) and 0.1 g of SPAN 80 (sorbitan monooleate marketed by ICI (UK)), with the aid of an ultrasonic homogenizer. This inverse emulsion was put into a thermo-controlled 50 ml glass reactor fitted with a mechanical stirrer and a condenser. 2 g of methyltrimethoxysilane (MTMS) was introduced and stirring of the mixture was continued for 6 hours at 20° C. The water present in the emulsion was then removed by azeotropic distillation. The solids content of the organic suspension was 2.95% by weight, which corresponds to a polycondensation yield of close to 100%, expressed as weight of poly(methyl)silsesquioxane formed.

The iron oxide content of the particles was 35%, estimated by atomic absorption. The magnetic pigment was uniformly distributed throughout the volume of the sphere, as shown by the view given by transmission electron microscopy, using a scale of 0.09 micron. The particle sizes were between 0.05 micron and 0.5 micron.

These same particles were collected by magnetization and redispersed in water in the presence of Cemulsol NP30 (ethoxylated nonylphenol containing 30 molecules of ethylene oxide, marketed by SFOS (France)) in a concentration of 1 g/l to form a magnetic latex having a solids content of 10%.

EXAMPLE 2

Example 1 was repeated except that Solvesso 200 was replaced with cyclohexane and SPAN 80 was replaced by Hypermer LP8 (a dispersing agent marketed by ICI (UK)). The yield, expressed as weight of poly(methyl)silsesquioxane formed, was close to 100%.

EXAMPLE 3

Example 1 was repeated except that Solvesso 200 was replaced with Garbexol A6 (an adipic acid diester marketed by SFOS (France)). The yield, expressed as weight of poly(methyl)silsesquioxane formed, was about 76%.

EXAMPLE 4

Example 1 was repeated replacing Solvesso 200 with octane. The 2 g of methyltrimethoxysilane (MTMS) were first introduced into the iron oxide suspension and stirred for a few minutes to hydrolyze the MTMS and to obtain a homogeneous suspension. The latter was then dispersed in octane and homogenized using ultrasonic sound. The emulsion in octane was stirred for one hour at 20° C. and a supplementary 2 g of MTMS were then introduced into the emulsion. The treatment was continued as indicated in Example 2. The yield, expressed as weight of poly(methyl)silsesquioxane formed, was close to 100%. The iron oxide content of the particles was 21%.

EXAMPLE 5

Preparation of Magnetizable Microspheres Based on Poly(vinyl)silsesquioxane

The conditions of Example 1 were employed, replacing MTMS with vinyltrimethoxysilane (VTMO). The yield, expressed as weight of poly(vinyl)silsesquioxane formed, was 67%. The iron oxide content of the particles was 43%.

EXAMPLE 6

Preparation of Magnetizable Microspheres Based on Poly(methacryloxypropyl)silsesquioxane The conditions of Example 1 were employed replacing MTMS with methacryloxypropyltrimethoxysilane (MEMO). The yield, expressed as weight of poly(methacryloxypropyl)-silsesquioxane formed, was 42%. The iron oxide content of the particles was 47%.

EXAMPLE 7

Preparation of Magnetizable Microspheres Based on Poly(glycidylproppl)silsequioxane The conditions of Example 1 were employed replacing MTMS with glycidylpropyltrimethoxysilane (GLYMO). The yield, expressed as weight of poly(glycidylpropyl)-silsesquioxane formed, was 19%. The iron oxide content of the particles was 66%.

EXAMPLE 8

Preparation of magnetizable microspheres based on poly(aminopropyl)silsesquioxane The conditions of Example 1 were employed replacing MTMS with aminopropyltrimethoxysilane (AMEO) and first introducing the AMEO into the aqueous suspension of iron oxide. This was accompanied by a transient flocculation of the suspension. The remainder of the treatment was continued as indicated in Example 1.

EXAMPLE 9

(Comparative Example for Example 1)

In this example the aqueous suspension of iron oxide, not treated with a surfactant, was replaced by a suspension of iron oxide treated with a surfactant and prepared by the process disclosed in U.S. Pat. No. 4,094,804. Iron oxide was precipitated in the presence of oleic acid, which was repeptized in an aqueous medium by adding an anionic emulsifier (dioctyl sulphosuccinate), Aerosol OT, marketed by American Cyanamid. The synthesis was continued by the same method as in Example 1. In this case magnetizable microspheres were not obtained; in fact, the iron oxide had diffused progressively from the aqueous phase towards the organic phase.

I claim:
1. Magnetizable microspheres comprising:
   a matrix based on a polysilsesquioxane network; and
   a magnetizable filler uniformly distributed inside said network and chemically bonded to silsesquioxane units, said filler having a size smaller than $300 \times 10^{-4}$ μm, said microspheres having a BET specific surface area ranging from 2 to 50 m²/g.
2. The microspheres according to claim 1, wherein the polysilsesquioxane is represented by the unit formula R—Si—$O_{3/2}$ and is obtained by polycondensation of an alkoxysilane of the formula:

or an alkoxysiloxane of the formula:

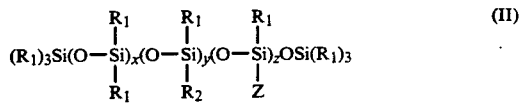

in which formulae:
   $R_1$ is selected from a $C_1$-$C_3$ alkyl radical, and a phenyl radical;
   $R_2$ is selected from a radical $R_1$, a $C_1$-$C_4$ substituted alkyl radical, and a vinyl radical;
   R is selected from a radical $R_1$, a radical $R_2$, an ethylenically unsaturated radical and a diorganopolysiloxy radical having from 4 to 20 diorganosiloxy groups;

OR' is selected from an OH radical and a hydrolyzable radical in which R' represents:

a $C_1$-$C_4$ alkyl radical, or a —CO—CH$_3$, —CO—C$_2$H$_5$, —CO—CH$_2$—CO—CH$_3$, —CH$_2$—CH$_2$OH, —CH$_2$CH$_2$—OCH$_3$ or —CH$_2$—CH$_2$—OC$_2$H$_5$ radical;

Z is a radical —r—Si(R$_1$)$_{3-n}$ (OR')$_n$ in which r is a $C_1$-$C_{18}$ alkylene group and n is an integer from 0 to 3; and x, y and z have values sufficient to ensure a viscosity lower than 100 mPas at 25° C., wherein x or y can independently be zero.

3. The microspheres according to claim 2, wherein r of the Z radical is a $C_2$-$C_6$ alkylene group.

4. The microspheres according to claim 1, wherein the amount of magnetizable filler is about 0.5 to 98% of the weight of the microspheres.

5. The microspheres according to claim 1, wherein the magnetizable filler has a size ranging from about $50 \times 10^{-4}$ to about $120 \times 10^{-4}$ microns.

6. The microspheres according to claim 1, wherein the diameter of the microspheres ranges from about 0.05 to 3 microns.

7. A process for the preparation of magnetizable microspheres, comprising:

dispersing in an organic solvent immiscible with water, an aqueous suspension of magnetizable filler, not coated with a dispersing agent, said filler having a size smaller than $300 \times 10^4$ μm;

dissolving in the organic phase of the dispersion obtained, an alkoxysilane or an alkoxysiloxane capable of undergoing polycondensation, to form a polysesquioxane;

subjecting said alkoxysilane or alkoxysiloxane to polycondensation, removing the water resulting from the polycondensation; and separating off the magnetizable microspheres.

8. The process according to claim 7, further comprising redispersing the separated magnetizable microspheres in water.

9. The process according to claim 7, wherein the alkoxysiloxane has the formula:

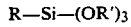  R—Si—(OR')$_3$          (I)

or the alkoxysiloxane has the formula:

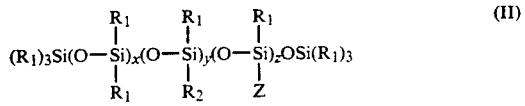

in which formulae:

R$_1$ is selected from a $C_1$-$C_3$ alkyl radical and a phenyl radical;

R$_2$ is selected from a radical R$_1$ defined above, a $C_1$-$C_4$ substituted alkyl radical, and a vinyl radical;

R is selected from a radical R$_2$ defined above, an ethylenically unsaturated radical, and a diorganopolysiloxy radical having from 4 to 20 diorganosiloxy groups;

OR' is selected from an OH radical and a hydrolyzable radical in which R' represents:

a $C_1$-$C_4$ alkyl radical, or a —CO—CH$_3$, —CO—CH$_2$H$_5$, —CO—CH$_2$—CO—CH$_3$, —CH$_2$—CH$_2$OH, —CH$_2$CH$_2$—OCH$_3$, or —CH$_2$—CH$_2$—OC$_2$H$_5$ radical;

Z is a radical —r—Si(R$_1$)$_{3-n}$ (OR')$_n$ in which r is a $C_1$-$C_{18}$ alkylene group and n is an integer from 0 to 3; and x, y and z have values sufficient to ensure a viscosity lower than 100 mPas at 25° C., wherein x or y can independently have a value of zero.

10. The process according to claim 9, wherein the r of the Z radical is a $C_2$-$C_6$ alkylene group.

11. The process according to claim 7, wherein the magnetizable filler has a size ranging from $50 \times 10^{-4}$ to $120 \times 10^{-4}$ microns.

12. The process according to claim 7, wherein the concentration of the dispersed magnetizable filler in the aqueous suspension ranges from about 0.5 to 50% by weight and the ratio by weight of the magnetizable filler to alkoxysilane or alkoxysiloxane ranges from about 0.005:1 to 50:1.

13. The process according to claim 7, wherein the amount of organic solvent used is such that the ratio, by weight, of the aqueous phase to the organic phase ranges from about 0.005:1 to 2:1.

14. A support for a biological or chemical substance comprising the magnetizable microspheres according to claim 1.

* * * * *

UNITED STATES PATENT AND TRADEMARK OFFICE
CERTIFICATE OF CORRECTION

PATENT NO. : 5,128,204

DATED : July 7, 1992

INVENTOR(S) : Dominique Charmot

It is certified that error appears in the above-identified patent and that said Letters Patent is hereby corrected as shown below:

claim 7, column 7, line 30, change "$300 \times 10^4 \mu m$" to --$300 \times 10^{-4} \mu m$--.

claim 9, column 7, line 44, change "alkoxysiloxane" to --alkoxysilane--; and column 8, line 20, change "$-CO-CH_2H_5$" to -- $-CO-C_2H_5$ --.

Signed and Sealed this

Fifth Day of October, 1993

*Attest:*

BRUCE LEHMAN

*Attesting Officer*   *Commissioner of Patents and Trademarks*